United States Patent [19]

Vercimak et al.

[11] Patent Number: 5,290,277

[45] Date of Patent: Mar. 1, 1994

[54] MULTI-FIBER LINEAR ARRAY LASER CATHETER CONNECTOR

[75] Inventors: Charmaine Vercimak, Coon Rapids; Steven D. Savage, Brooklyn Center; Gregory G. Brucker, Minneapolis, all of Minn.

[73] Assignee: Angeion Corporation, Minneapolis, Minn.

[21] Appl. No.: 863,098

[22] Filed: Apr. 3, 1992

[51] Int. Cl.$^5$ .............................................. A61B 17/36
[52] U.S. Cl. ..................................... 606/15; 385/115; 606/2
[58] Field of Search ................. 606/2, 3, 7, 9, 14–17; 385/115, 88, 89, 92, 93, 99

[56] References Cited

U.S. PATENT DOCUMENTS

| | | | |
|---|---|---|---|
| 2,354,931 | 8/1944 | Tolman | 385/115 X |
| 3,940,608 | 2/1976 | Kissinger et al. | 385/115 |
| 4,383,729 | 5/1983 | Suzuki et al. | 606/15 X |
| 4,547,040 | 10/1985 | Yamamoto et al. | 385/115 X |
| 4,570,063 | 2/1986 | DeBie et al. | 385/115 X |
| 5,034,010 | 7/1991 | Kittrell et al. | 606/15 |
| 5,066,292 | 11/1991 | Müller et al. | 606/15 X |

Primary Examiner—Peter A. Aschenbrenner
Attorney, Agent, or Firm—Patterson & Keough

[57] ABSTRACT

A multi-fiber linear array laser catheter for use in irradiation of biological tissue where a circular laser beam is optically transformed to coincide with the cross-section of a linear array of optical fibers. The transformed laser beams are focused onto a linear connector and transmitted through a plurality of parallel optical fibers. Heat is extracted and drawn from the vicinity of the parallel optic fibers by metallic plates acting as heat sinks on opposing sides of the parallel optic fibers.

15 Claims, 2 Drawing Sheets

MULTI-FIBER LINEAR ARRAY LASER CATHETER CONNECTOR

CROSS REFERENCES TO CO-PENDING APPLICATIONS

U.S. patent application Ser. No. 07/608,281, filed Nov. 2, 1990, and U.S. patent application Ser. No. 07/608,290, filed Nov. 2, 1990, are commonly assigned to the assignee of the present invention.

BACKGROUND OF THE INVENTION

1. Field of the Invention

The present invention generally pertains to medical and surgical apparatus, and more particularly, pertains to laser ablation catheters.

2. Description of the Prior Art

It is known in the art to use laser energy for medical purposes. A common medical application is in the irradiation of biological tissue. For external use, the laser energy may be directly applied. However, when the procedure requires irradiation of tissue which is not readily accessible, the use of a laser catheter is common. A typical application for a laser catheter is in the cardiovascular system. U.S. Pat. Nos. 4,997,431 and 4,985,028, both issued to Isner et al., show laser catheters particularly adapted for laser ablation within the cardiovascular system.

Multi-fiber systems have been particularly important in medical applications where laser energy must be transmitted from the laser power source to some location inside the human body. These configurations are needed to maintain a small diameter catheter for percutaneous introduction while providing a flexible catheter to negotiate the tortuous pathways in the cardiovascular system. However, when the medical applications require substantial laser power to be delivered over long periods of time, the traditional connector systems, such as described in U.S. Pat. No. 4,526,170, issued to Tanner, have proven inadequate.

U.S. Pat. No. 4,383,729, issued to Suzuki et al., shows a multi-fiber connector wherein a single beam of energy is split into component parts for transmission along a multiple fiber cable. However, such connectors may have difficulty handling the energy which is not intercepted by the optical fibers, and as a result the connector may be thermally damaged.

SUMMARY OF THE INVENTION

The current invention overcomes the inadequacies of the prior art by providing a connector designed to handle such energy requirements by refocusing a single generated laser beam into a line, and aligning the receiving array of fibers within the connector into a corresponding line to provide a highly efficient transfer of the laser energy. The individual fibers are arranged to be physically touching. The connector space not occupied by the fibers is packed with a reflective and/or refractive filler to redirect any spilled over energy into one or more of the fibers or to the outside surface of the connector.

According to one embodiment of the present invention, a 400 micron input fiber connects a laser interface module with a commercially available Nd:Yag medical laser. Multiple lenses contained within the interface box then transform a highly focused circular laser beam into a thin rectangular beam, whose dimensions are those of the fiber portion of the linear connector, and whose divergence is suitable for acceptance by the array fibers. The linear connector intercepts most of the laser energy, and that which is incident upon the optical fibers is transmitted to the distal end of the laser catheter through the multi-fiber bundle. The energy not directly intercepted by the fibers impinges upon an index matching epoxy filler that is transparent to the laser energy wavelength in the connector, which transmits this laser energy after multiple reflections to one or more of the multiple fibers or the surrounding metallic members in the multi-fiber linear array. The thermal energy not finally transferred in this way via the multi-fiber array is dissipated from the outside of the connector.

The multi-fiber linear array consists of multiple fibers aligned in a plane so that their diameters touch. The multiple fibers are bonded with an index-matching epoxy to a highly conductive external metal holder, such as aluminum or copper.

One significant aspect and feature of the present invention is a laser catheter with a multi-fiber linear array connector.

Another significant aspect and feature of the present invention is a multi-fiber linear array laser catheter connector with a lens system.

Another significant aspect and feature of the present invention is a multi-fiber linear array laser catheter connector which can be used for extended periods of time without additional cooling devices.

Having thus described one embodiment of the present invention, it is the principal object hereof to provide a laser catheter with a multi-fiber linear array connector to couple and conduct higher power for extended periods of time for irradiating biological tissue.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DESCRIPTION OF THE PREFERRED EMBODIMENTS

Figure 1:
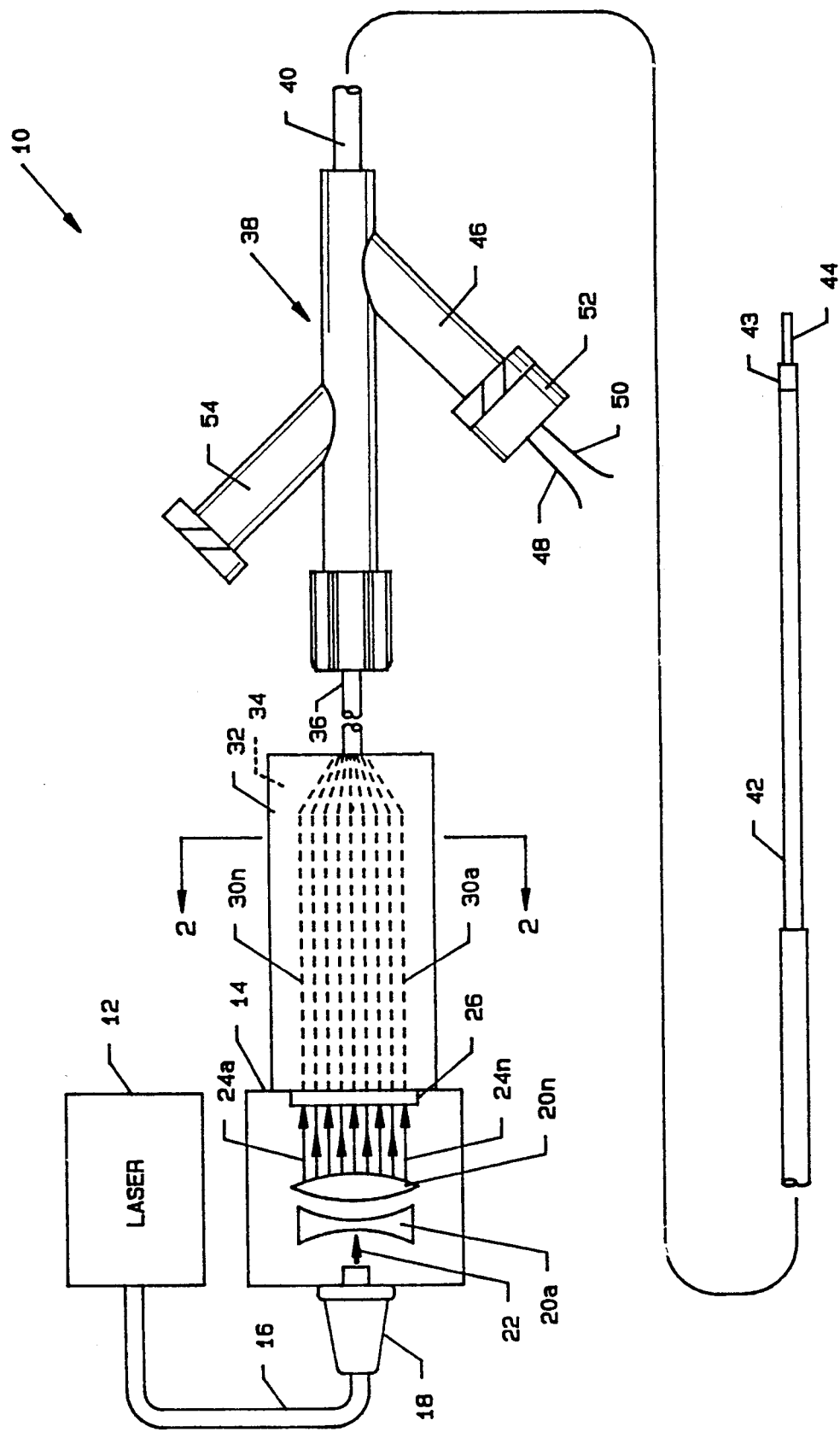
FIG. 1 illustrates a plan view of the multi-fiber linear array laser catheter, the present invention; and, FIG. 2 illustrates a cross-sectional view of the fiber linear array along line 2—2 of FIG. 1.

FIG. 1 illustrates a plan view of the fiber optic linear array laser catheter 10, the present invention. A laser 12 connects to a laser interface module 14 via an input fiber 16 and a fiber connector 18. The laser interface module 14 includes a plurality of lenses, including lenses 20a–20n, which transform a highly focused laser beam 22 into a thin rectangular beam illustrated by arrows 24a–24n, whose dimensions are those of the fiber portion of a linear connector 26. A fiber optic linear array 28 (FIG. 2) aligns in and connects to the linear connector 26, and includes a plurality of single optical fibers 30a–30n aligned in a planar fashion. The fiber optic linear array 28 includes highly thermally conductive plate members 32 and 34, such as aluminum or copper members, aligned about the array of single optical fibers 30a–30n. The linear connector 26 intercepts incident laser energy, and transmits it through the optical fibers of fiber optic linear array 28. Laser energy, which is incident upon the single optic fibers 30a–30n, is delivered to the distal end of the linear array laser catheter 10. Laser energy, which is not intercepted by the individual optic fibers 30a–30n, impinges upon an index-matching epoxy 56 (see also FIG. 2) which serves as a filler between conductive plates 32 and 34 of linear array 28. After multiple reflections, this energy is either transferred to one of the individual optical fibers or is transferred to the metallic heat conductive plates 32 and 34 of the fiber optic linear array 28, which simultaneously store and transmit the thermal energy to the ambient.

The single optical fibers 30a–30n are necked down in the fiber optic linear array 28 to form a fiber optic cable 36, which ring a central lumen in a Y-connector 38. The fiber optic cable 36 is routed through the Y-connector 38, a stainless steel tubular member 40, and a plastic tube 42 to a tubular tip 43, which can be made of metal for electrical conduction if desired. A fixation wire 44, which may include temperature sensing members, such as thermocouples, extends from the tubular tip 43 and is routed through the plastic tube 42, the stainless steel tubular member 40, and the Y-connector 38. Wires 48 and 50 connect to the temperature sensors on the fixation wire 44 and exit the port 46 on the Y-connector 38. Tubular tip 43 is electrically connected to a conducting metallic plug 52 located at the end of the Y-connector port 46. A flushing port 54 extends from the body of the Y-connector 38.

The energy transmitted by the fibers can be directed in a number of ways to irradiate human tissue. The fibers may be canted at a small angle to the axis of the catheter to achieve divergence of the laser energy beyond that which is available due to the intrinsic nature of the numerical aperture of the fiber. Alternatively, the distal ends of the fibers may be polished non-flat to create a prism to bend the light. The interstitial spaces between the fibers is used for irrigating fluid to remove biological materials from the field of the laser light and to cool the tissue so that local carbonization of the tissue does not occur.

Figure 2:
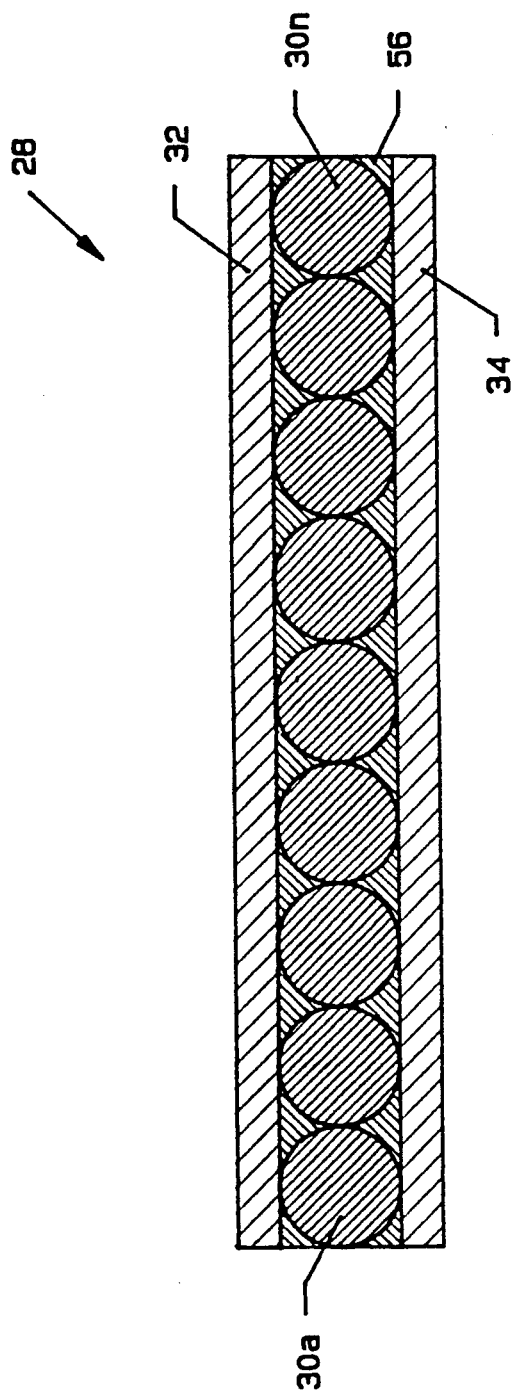

FIG. 2 illustrates a cross-sectional view of the fiber optic linear array 28 along line 2—2 of FIG. 1 where all numerals correspond to those elements previously described. Single optical fibers 30a–30n are aligned such that their diameters touch and are bonded to the highly conductive plates 32 and 34 by an index-matching epoxy 56. Heat from the single optic fibers 30a–30n is transmitted through the index-matching epoxy 56 to the highly conductive plates 32 and 34 from where the heat is dissipated.

MODE OF OPERATION

In application, a highly focused circular laser beam is optically transformed into a linear beam of the same dimension as the linear array of fibers, and is focused onto the linear connector. The energy which is intercepted by the fibers is then transmitted by the optical fibers of the linear array to the distal end of the catheter, while the remaining energy is intercepted by the epoxy and transmitted via optical reflection or refraction to the surrounding conductive plates 32 and 34 of the multi-fiber linear array connector. Because of the high thermal conductivity of the metal, its large heat capacitance, and large surface area, the heat is dissipated before the temperature becomes high enough to cause optical misalignment or structural degradation of the fibers. This allows the system to maintain structural integrity and optical alignment under high power conditions for long periods of time.

The advantage of the multi-fiber linear array laser catheter is that continuous high power can be delivered for long periods of time without active cooling or specialized energy management strategies with respect to the laser. Thus, for medical applications, such as treatment of ventricular tachycardia, the limitation of the low input power or highly focused laser energy profiles are no longer present.

Various modifications can be made to the present invention without departing from the apparent scope hereof.

We claim:

1. An apparatus comprising:
   a. means for generating a beam of laser energy;
   b. means coupled to said generating means for transferring said beam of laser energy;
   c. means coupled to said transferring means for transforming said beam of laser energy into a line of laser energy having a first width and a first length.
   d. linear array means coupled to said transforming means for coupling said line of laser energy to a plurality of optical fibers; said linear array means comprising a connector housing comprising a plurality of outer metal plates and filler material comprising index matching epoxy located between said metal plates and positioned around the optical fibers, the metal plates having a high thermal conductivity suitable for rapid external dissipation of heat from within the connector housing to prevent optical misalignment and degradation of optical fibers; and,
   e. a medical catheter located about said plurality of optical fibers for housing said plurality of optical fibers.

2. An apparatus according to claim wherein each of said plurality of optical fibers has a proximal end and a distal end and said proximal ends of said plurality of optical fibers are arranged in a line.

3. An apparatus according to claim 2 wherein said proximal ends of corresponding ones of said plurality of optical fibers are in contact with corresponding other ones of said plurality of optical fibers.

4. An apparatus according to claim 1 wherein said connector housing comprises a first plate along one side of said line and a second plate along the other side of said line.

5. An apparatus according to claim 1 wherein said transforming means comprises a lens.

6. An apparatus according to claim 5 wherein said transforming means further comprises a plurality of lenses.

7. An apparatus according to claim 6 wherein said first width is approximately equal to the width of said line.

8. An apparatus according to claim 7 wherein said first length is approximately equal to the length of said line.

9. A method of coupling a medical laser energy generator to a plurality of optical fibers within a medical catheter comprising:
   a. transforming the output of said laser generator to a line of laser energy;
   b. arranging the proximal ends of said plurality of optical fibers in an index matching epoxy surrounded by a plurality of metal plates to receive said line of laser energy; and, c. positioning said arranged proximal ends of said plurality of optical fibers in alignment with said line of laser energy.

10. A method according to claim 9 further comprising locating said arranged proximal ends of said plurality of optical fibers within a connector housing.

11. A laser catheter comprising:

a. means for generating a laser beam;

b. means for transporting said laser beam to a laser interface module;

c. a linear connector comprising a plurality of optical fibers, an index matching epoxy filler between the interstices of said plurality of optical fibers, and metal heat dissipator means; and, d. means for refocusing said cylindrical laser beam into a thin rectangular beam aimed to impinge said linear connector.

12. The laser catheter of claim 11 wherein any portion of said refocused laser beam not impinging said plurality of optical fibers in said linear connector impinges said matching epoxy filler.

13. The laser catheter of claim 12 wherein said laser catheter has a proximal end and a distal end, said proximal end being coupled to said laser interface module, and wherein said refocused laser beam impinging said plurality of optical fibers is delivered to said distal end of said laser catheter.

14. The laser catheter of claim 12 wherein the thermal energy from said refocused laser beam impinging said matching epoxy filler is dissipated by said heat dissipator means.

15. An apparatus according to claim 4 wherein the metal is selected from the group consisting of aluminum and copper.

* * * * *

UNITED STATES PATENT AND TRADEMARK OFFICE
CERTIFICATE OF CORRECTION

PATENT NO. : 5,290,277
DATED : March 1, 1994
INVENTOR(S) : Vercimak, et al.

It is certified that error appears in the above-indentified patent and that said Letters Patent is hereby corrected as shown below:

Column 4, line 39 add --1-- after the word "Claim"

Signed and Sealed this

Twenty-ninth Day of November, 1994

Attest:

BRUCE LEHMAN

Attesting Officer

Commissioner of Patents and Trademarks